United States Patent [19]
Varshavsky et al.

[11] Patent Number: 6,159,732
[45] Date of Patent: Dec. 12, 2000

[54] NUCLEIC ACID ENCODING MAMMALIAN UBR1

[75] Inventors: Alexander Varshavsky, La Canada Flintridge; Yong Tae Kwon, Pasadena, both of Calif.

[73] Assignee: California Institute of Technology, Pasadena, Calif.

[21] Appl. No.: 09/228,317

[22] Filed: Jan. 11, 1999

Related U.S. Application Data

[62] Division of application No. 08/982,956, Dec. 2, 1997, Pat. No. 5,861,312.

[51] Int. Cl.[7] ........................................... C12N 5/00

[52] U.S. Cl. ............................ 435/325; 435/252.3; 435/6; 536/23.1; 536/24.3

[58] Field of Search ................................ 435/325, 252.3, 435/6; 536/23.1, 24.3

[56] References Cited

PUBLICATIONS

Wallace Robert W, "Does antisense make sense?", DDT, 1/99, vol. 1, pp. 4–5.

Agrawal, S., "Antisense oligonucleotides: twoards clinical trials", Trends in Biotechnology, 10/96, vol. 14, No. 10, pp. 376–87.

*Primary Examiner*—John S. Brusca
*Assistant Examiner*—Stephen Siu
*Attorney, Agent, or Firm*—Kevin M. Farrell

[57] ABSTRACT

Disclosed here is a nucleic acid sequence encoding a recognition component of the N-end rule pathway. This nucleic acid sequence is characterized by the ability to specifically hybridize to the nucleic acid sequence of SEQ ID NO 1 under stringent hybridization conditions. Such conditions are defined below. Also disclosed is a nucleic acid sequence encoding a recognition component of the N-end rule pathway which is characterized by the ability to specifically hybridize to the nucleic acid sequence of SEQ ID NO 2 under stringent hybridization conditions. Also disclosed are DNA expression vectors containing nucleic acid sequences of the type described above, as well as cells transformed with such expression vectors. Further disclosed are applications for the compositions described above.

8 Claims, 1 Drawing Sheet

NUCLEIC ACID ENCODING MAMMALIAN UBR1

RELATED APPLICATIONS

This application is a Divisional of prior U.S. application Ser. No. 08/982,956 filed Dec. 2, 1997 (now U.S. Pat. No. 5,861,312).

GOVERNMENT SUPPORT

This invention was made with government support under Grant #DK 39250 awarded by the National Institutes of Health. The government has certain rights in the invention.

BACKGROUND OF THE INVENTION

Features of proteins that confer metabolic instability are called degradation signals, or degrons (Varshavsky, *Cell* 64: 13–15 (1991)). The essential component of one degradation signal, termed the N-degron, is a destabilizing N-terminal residue of a protein (Bachmair, et al., *Science* 234: 179–186 (1986)). A set of N-degrons containing different destabilizing residues is referred to as the N-end rule, which relates the in vivo half-life of a protein to the identity of its N-terminal residue (for review see Varshavsky, *Cell* 69: 725–735 (1992) and Varshavsky, *Cold Spring Harbor Symp. Quant. Biol.* 60: 461–478 (1996)). The N-end rule pathway has been found in all species examined, including the eubacterium *Escherichia coli*, the yeast *Saccharomyces cerevisiae*, and mammalian cells. The N-end rules of these organisms are similar but distinct.

As discussed in greater detail below, ongoing studies have revealed that the N-end rule pathway participates in a variety of complex functions in eukaryotic systems. Such studies indicate that the ability to intervene at the molecular level to inhibit or modulate the N-end rule pathway offers an important therapeutic avenue. Given the relatively complex enzymology of the pathway, the availability of components in quantity is essential to the development of therapeutic methods.

SUMMARY OF THE INVENTION

The subject invention relates, on one aspect, to a nucleic acid sequence encoding a recognition component of the N-end rule pathway. This nucleic acid sequence is characterized by the ability to specifically hybridize to the nucleic acid sequence of SEQ ID NO 1 under stringent hybridization conditions. Such conditions are defined below. In another aspect, the invention relates to a nucleic acid sequence encoding a recognition component of the N-end rule pathway which is characterized by the ability to specifically hybridize to the nucleic acid sequence of SEQ ID NO 2 under stringent hybridization conditions. Other embodiments relate to DNA expression vectors containing nucleic acid sequences of the type described above, as well as cells transformed with such expression vectors. The invention also relates to applications for the compositions described above.

DETAILED DESCRIPTION OF THE INVENTION

Figure 1:
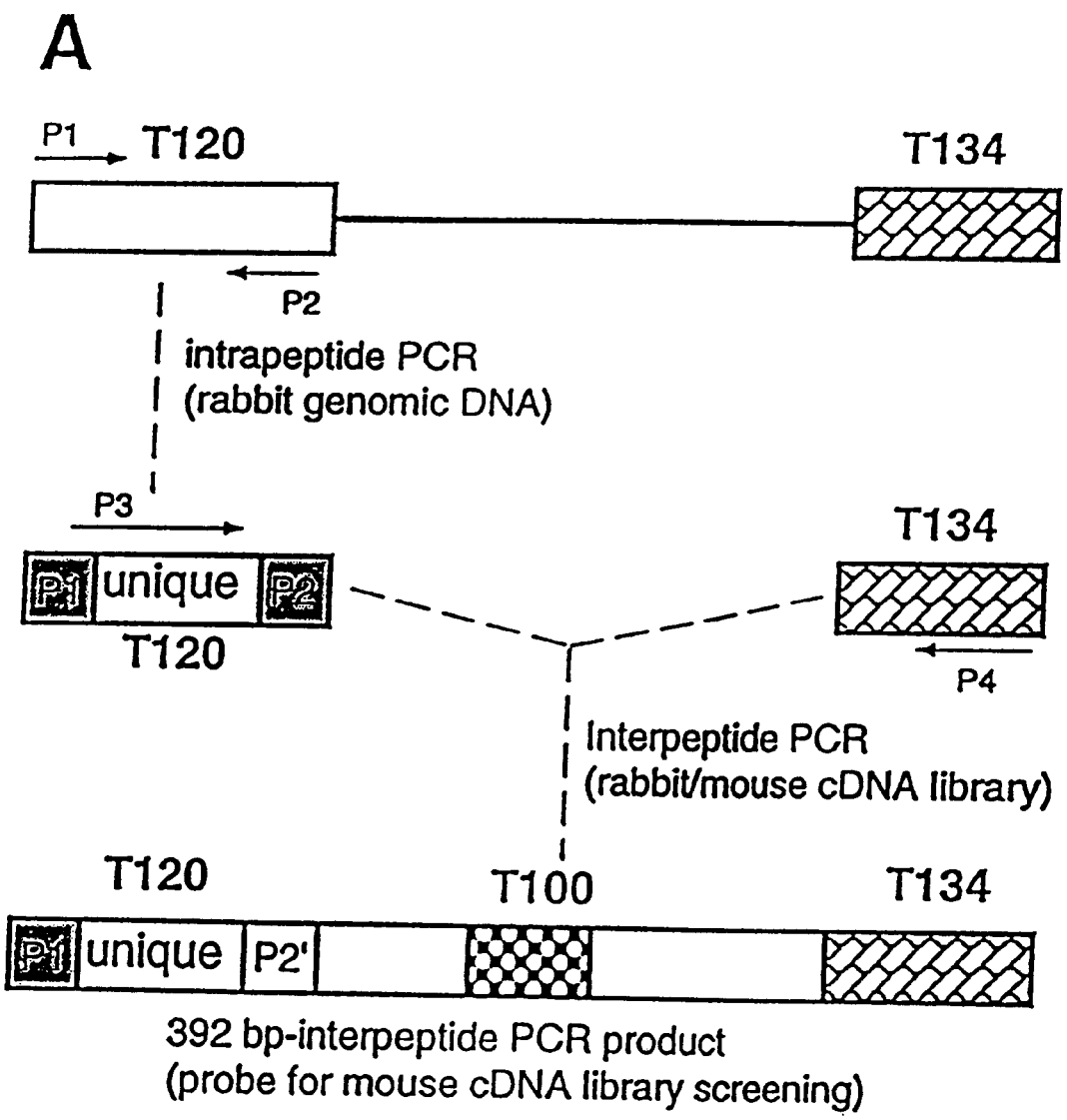
FIG. 1 is a diagrammatic representation of the strategy employed for the cloning of mouse Ubr1 cDNA by intrapeptide PCR, interpeptide PCR, followed by conventional library screening.

The present invention is based on the isolation and cloning of nucleic acids encoding both human and murine forms of the recognition component of the N-end rule pathway, Ubr1. Ubr1, also referred to as E3α, is a ubiquitin-protein ligase which has been linked, in particular, to stress-related deterioration (wasting) of muscle tissue.

More specifically, the rapid loss of muscle proteins associated with a variety of disease states has been shown to be primarily due to enhanced proteolysis via the ubiquitin-proteasome pathway (Mitch and Goldberg, *N. Eng. J. Med.* 335: 1897 (1996)). In rabbit skeletal muscle extracts, the N-end rule pathway is the dominant pathway for protein degradation—catalyzing the complete degradation of soluble proteins to amino acids (Solomon et al., *J. Biol. Chem.* 271: 26690 (1996)). In soluble extracts of rabbit muscle tissue, known inhibitors of the Ubr1 gene product were demonstrated to reduce the ATP-dependent degradation of soluble muscle proteins to amino acids by blocking their conjugation to $^{125}$I-ubiquitin (Solomon et al., Abstracts from 1997 FASEB Summer Meeting, Vermont (1997)).

Solomon et al. (Abstracts from 1997 FASEB Summer Meeting, Vermont (1997)) also report the identification of changes in the rate of protein ubiquitination associated with a number of pathological states characterized by muscle proteolysis. More specifically, in atrophying rat muscles, when overall protein degradation increases (e.g., in septic rats with sepsis induced by cecal puncture), hyperthyroid rats (treated with triiodothyronine) or in tumor-bearing rats (carrying Yoshida Ascites Hepatome for 3 to 5 days)), $^{125}$I-ubiquitin conjugation to soluble proteins increased 2-fold above the levels found in control muscles. Introduction of a known inhibitor was found to selectively suppress the increased $^{125}$I-ubiquitin conjugation toward levels in control muscles. In addition, ubiquitination of $^{125}$I-lysozyme (a model N-end rule substrate) was also determined to increase by 2-fold in extracts of atrophying muscles above levels in control extracts. Following hypophysectomy or thyroidectomy, protein degradation was shown to fall in isolated rat muscles. In extracts of such muscles, $^{125}$-I-ubiquitin conjugation to soluble proteins also falls by 50% in parallel with protein degradation. Addition of the lysine-alanine dipeptide suppressed $^{125}$I-ubiquitin conjugation to soluble proteins and eliminated most of the differences in this process between control and hypophysectomized or thyroidectomized rat muscle extracts. Ubiquitination of $^{125}$I-lysozyme was also reduced in these extracts indicating that the activities of components of the N-end rule pathway fall in muscles of thyroidectomized and hypophysectomized rats.

Observations such as those set forth above suggest that inhibitors of the N-end rule pathway will prove useful in connection with the treatment of various diseases characterized by the wasting of muscle tissue. While certain inhibitors of the N-end rule pathway are known (e.g., dipeptides resembling substrates of the N-end rule) the in vivo utility of such inhibitors is limited. Thus, one aspect the present invention relates to methods and compositions for inhibiting the N-end rule pathway-mediated muscle deterioration.

In addition to the treatment of various diseases characterized by the wasting of muscle tissue, the inhibition of the N-end rule pathway is indicated as a means of intervention for treatment of infection by intracellular pathogens such as *Lysteria monocytogenes* and *Yersinia enterocolitica*. Intracellular pathogens of this type occupy the cytoplasm of an infected cell, and propagate without killing the cell. An organism attempts to rid itself of infection by such pathogens through degradation of the pathogen's constituent proteins intracellularly, followed by the presentation of bacterial protein fragments to the immune system of the host via the major histocompatibility complex (MHC) class I-associated cytolytic T lymphocyte epitopes.

A recent report by Sijts et al. (*J. Biol. Chem.* 272: 19261 (1997)) highlights the involvement of the N-end rule pathway in connection with the MHC-associated presentation of *Listeria monocytogenes* epitopes. More specifically, the investigators focused on the degradation of p60, a Listeria-secreted murein hydrolase. Roughly 3% of degraded p60 gives rise to p60 217–225, a nonamer peptide that is bound by H-2K$^d$ MHC class I molecules. Mutagenesis of the N-terminal residue of p60 to replace the wild-type residue with amino acids known to be either stabilizing or destabilizing according to the N-end rule demonstrated clearly that p60 is a substrate of the N-end rule pathway. Valine substitution dramatically stabilized cytosolic p60 molecules, whereas aspartic acid substitution resulted in rapid degradation.

Cytosolic antigen degradation is fundamental to the generation of most MHC class I presented peptides. The fact that such degradation is, in the case of intracellular pathogens, mediated by the N-end rule pathway, strongly suggests intervention and manipulation of the pathway can be used to treat such infections. While the definitive demonstration of the importance of the N-end rule pathway in the life cycle of an invading bacterium such as *L. monocytogenes* remains to be demonstrated directly, the basis for the comments relating to therapy is the fact that intracytosolic parasites such as *L. monocytogenes* co-evolved with the N-end rule pathway. Therefore, drug-mediated perturbations of this pathway (either its inhibition or activation) are extremely likely to influence the course of infection by these bacteria.

Discussed above are examples of two pathological states, stress-induced deterioration of muscle tissue and infection by an intracellular pathogen, which are amenable to treatment by molecular intervention involving the N-end rule pathway. The N-end rule pathway has been well-studied and is the subject of several comprehensive review articles (see e.g., Varshavsky, *Trends Biochem. Sci.* 22: 383 (1997) and Varshavsky, *Proc. Natl. Acad. Sci. USA* 93: 12142 (1996)).

A brief review of the enzymology of the N-end rule pathway is warranted. Eukaryotic cells contain ubiquitin-specific enzymes that catalyze reactions whose product is either a single ubiquitin moiety or a multi-ubiquitin chain covalently linked to an acceptor protein. Ubiquitin is conjugated to other proteins through an amide bond, called the isopeptide bond, between the C-terminal (Gly-76) residue of ubiquitin and the ε-amino group of a lysine residue in an acceptor protein.

Ubiquitin is activated for conjugation to other proteins by a ubiquitin-activating enzyme (E1), which couples ATP hydrolysis to the formation of a high-energy thioester bond between Gly-76 of ubiquitin and a specific cysteine residue of E1. The E1-linked ubiquitin moiety is moved, in a transesterification reaction, from E1 to a cysteine residue of a ubiquitin-conjugating enzyme (E2), and from there to a lysine residue of an ultimate acceptor protein, yielding a ubiquitin-protein conjugate. This last step requires the participation of another component, called E3 or recognin, which selects a protein for ubiquitylation through an interaction with its degradation signal. Ubr1p, the E3 of the N-end rule pathway, is a bona fide enzyme that acts at the step between an E2 and an ultimate acceptor of ubiquitin. It catalyzes the movement, through transesterification, of the ubiquitin moiety from the cysteine residue of a relevant E2 enzyme to a cysteine residue of E3 itself.

Ultimately, ubiquitin-protein conjugates generated by the cascade of enzyme-catalyzed reactions described above, are specifically degraded by an approximately 2,000 kDa, ATP-dependent protease, termed the 26S proteasome. The 26 S proteasome consists of a 20S core proteasome and a complex containing multiple ATPases at both ends of the 20S proteasome.

Ubr1 is one of several E3-type proteins of the ubiquitin system. Ubr1 is specific, in particular, for "destabilizing" residues exposed at the N-terminus of protein substrates. Since the degradation signals recognized by Ubr1 represent only a relatively small subset of the signals recognized by the entire ubiquitin system, inhibition of Ubr1 (and hence inhibition of the N-end rule pathway) would be a relatively mild, non-lethal therapeutic intervention, whereas the inhibition of the entire ubiquitin system would be lethal in mammalian cells, and therefore undesirable for selective therapy.

Inhibition of the Ubr1-encoded function in a cell can be effected in a variety ways. For example, at the nucleic acid level, an inhibitory molecule which specifically hybridizes to the Ubr1 mRNA can be contacted with the Ubr1 mRNA under physiological conditions, thereby inhibiting translation of the Ubr1 mRNA. Alternatively, inhibitors of the translated Ubr1 gene product can be introduced. With respect to inhibition at the translation level, knowledge of the Ubr1 cDNA sequence is essential. With respect to inhibition of the translated Ubr1 gene product, the availability of a cloned nucleic acid sequence encoding Ubr1 is a virtual necessity, for example, for the production of quantities of Ubr1 necessary for screening assays.

Thus, in one aspect, the present invention relates to a nucleic acid sequence encoding the Ubr1 recognition component of the N-end rule pathway. Disclosed herein are cDNA sequences corresponding to murine and human forms of Ubr1.

Given the nucleic acid sequences provided herein, one of skill in the art using no more than routine experimentation could isolate full length cDNAs from virtually any mammalian source. These cDNAs could be inserted into eukaryotic or prokaryotic expression vectors for the production of Ubr1 using recombinant DNA techniques. The scope of Applicants' invention is not limited to the specifically disclosed sequences, but rather encompass variations of such sequences which: 1) hybridize to the disclosed sequences under stringent hybridization conditions; and 2) encode a functional Ubr1 protein. With respect to the first criteria, an example of stringent hybridization conditions includes hybridization in which the disclosed sequences (or a portion thereof) are fixed to a solid support and a second DNA molecule to be tested for the ability to hybridize to the disclosed sequences is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.). With respect to the second criteria, the functionality of an encoded product can be determined by a variety of assay techniques including, for example, any of the in vitro techniques discussed below.

Inhibition of Ubr1 mRNA translation may be effected by introducing oligonucleotides, or oligonucleotide combinations into a cell of interest. Alternatively, an antisense gene construct encoding a transcription product which is complementary with at least a portion of the Ubr1 mRNA may be employed. Due to the inherent difficulties associated with the introduction of oligonucleotides into the cells of an organisms, the use of an antisense gene construct is preferred in a therapeutic context. An antisense gene construct may be produced, for example, by inserting at least a portion of double-stranded Ubr1 cDNA into an expression vector in reverse orientation, as compared to the wild-type context, relative to a promoter. The expression vector is selected to be suitable for use in the target cell type. For use in connection with therapy in humans, eukaryotic virus-based vectors are preferred. Preferably, the nucleic acid encoded by the reverse gene construct is complementary with the Ubr1 mRNA in a region known to be critical with respect to expression. Typically, initial designs include translation start sites, splice junctions, and other sites critical with respect to expression.

As an alternative to the inhibition of translation of the Ubr1 mRNA, strategies designed to inhibit the activity of the translated Ubr1 gene product are employed. For example, contacting the expressed Ubr1 gene product with a molecule which specifically binds to the Ubr1 gene product and inhibits its activity is a preferred method of inhibition.

A variety of methods may be employed to identify a specific inhibitor of the Ubr1 gene product. For example, using a DNA expression vector containing expressible Ubr1 cDNA, the Ubr1 gene product may be overexpressed in vitro. The in vitro system is supplemented with the relevant ubiquitin conjugating enzyme (E2), the mammalian ubiquitin activating enzyme (E1), free ubiquitin and ATP in amounts sufficient to support ubiquitylation of substrates of the N-end rule pathway. Once established, this in vitro system is employed to screen small molecule libraries for the identification of inhibitors which exert their effect in an ATP and Ubr1-dependent manner. Such small molecule libraries are assembled from sources rich in complex small organic molecules. Bacterial and plant cell extracts are frequently used sources for the isolation of a large number of diverse organic molecules for such screening purposes.

Another method suitable for the identification of a specific inhibitor of the Ubr1 gene product involves the overexpression of the Ubr1 gene product in a mammalian cell line. Again, an expression vector is carefully selected to be compatible with the preferred mammalian cell line. In preferred embodiments, the cell line employed is a human cell line. The overexpression of the Ubr1 gene product in the mammalian cell line would increase the activity of the N-end rule pathway in the cell culture. In such a Ubr1-enhanced assay, inhibitors are detectable at a far greater level of sensitivity than would otherwise be provided by a wild-type cell line.

The availability of the Ubr1 cDNA sequence also provides the opportunity for the identification of specific inhibitors by a rational approach based on a complete understanding of the Ubr1 atomic architecture. The availability of the Ubr1 cDNA enables the production of the Ubr1 gene product by recombinant DNA techniques in milligram quantities. The recombinantly produced Ubr1 gene product can be crystallized, and its structure determined at atomic resolution by X-ray diffraction techniques. Using such techniques in combination with conventional molecular modelling, rationally designed candidate inhibitor molecules, designed to interact with specific subdomains of the Ubr1 gene product are designed and tested.

EXEMPLIFICATION

Materials and Methods i) peptide preparation and sequencing.

Rabbit Ubr1 protein (previously termed E3α) was purified from reticulocyte lysate using immobilized-protein column and elution by dipeptides as described (Reiss and Hershko, J. Biol. Chem 265: 3685–3690 (1990)). The sample containing approximately 20 μg (~100 pmol) of the purified Ubr1 protein and chicken ovalbumin as a stabilizer for Ubr1 activity, in 50 mM N-ethyl morpholine, pH 8.5, 0.2 mM $CaCl_2$ and 10% isopropanol, was digested with trypsin at an enzyme-substrate mass ratio of 1:20 at ambient temperature for 24 hrs. The digested sample was dried and resuspended in 6M guanidine-HCl, 0.1% trifluroacetic acid (TFA). The tryptic peptides were fractionated by reverse-phase HPLC on a C18 column and eluted with a gradient of acetonitrile in 0.1% TFA. The isolated peptides were sequenced by automated Edman degradation on a model 470A/900/120A gas phase sequencer/on-line analyzer (Applied Biosystems) using standard chemistry. Fourteen sequences of different peptides were obtained.

ii) Intrapeptide and interpeptide PCR.

Based on the rabbit Ubr1 peptide sequences, the intrapeptide PCR with degenerate oligonucleotides using rabbit genomic DNA (Clontech) as a template was applied to amplify the unique rabbit Ubr1 cDNA sequence corresponding to the internal region of the two PCRs (FIG. 1). Specifically, immediately prior to initiation of the PCR reaction, PCR primers were boiled for 1 min. and immediately cooled on ice. The PCR premixtures (100 μl reaction volume) without AmpliTaq DNA polymerase were preincubated at 72° C. (3 min.) in GeneAmp PCR System 9600 (Perkin-Elmer) and then AmpliTaq polymerase was added to each tube containing the premixture. After 94° C. for 2 min., the first 4 cycles were done at 94° C. for 1 min., 65° C. for 10 min., and 72° C. for 1 min. In the following 20 cycles, the factors in PCR were gradually decreased every four cycles; the denaturation time to 50, 30, 25, 20, and 15 sec; the annealing temperature to 62, 58, 55, 50, and 45° C.; the annealing time to 5, 4, 3, 3, and 2 min.; and the extension time to 50, 30, 25, 25, and 25 sec. Then the final 20 cycles were done at 94° C. for 15 sec, 42° C. for 2 min., and 72° C. for 25 sec. The amplified intrapeptide PCR products were analyzed by electrophoresis in a 4% low melting temperature agarose gel, cloned into PCR2.1 vector (Invitrogen, CA) and screened by digestion with restriction enzymes and subsequent sequencing.

Three PCRs gave the intrapeptide PCR products which contained the expected deduced amino acid sequences. The PCR primer pairs used for the positive clones were designated as follows: T122 (forward and reverse); T120 (forward and reverse); and T96 (forward and reverse). These designations correspond to the designations assigned to 3 of the 14 rabbit peptide sequences determined as described above.

Subsequently, the oligonucleotides corresponding the unique sequence of the intrapeptide PCR products using rabbit liver cDNA library (Clontech) as a template were applied to get Ubr1 cDNA fragment between the two peptides (interpeptide PCR) (FIG. 1). Among many combinations of primers, an oligonucleotide containing the unique sequence of T120 and another degenerate oligonucleotide corresponding to T134 (another of the 14 rabbit peptide sequences determined) produced a 392 bp fragment. Subsequently, the 392 bp-mouse Ubr1 cDNA fragment corresponding to the 392 bp-rabbit Ubr1 cDNA fragment was obtained from the mouse cDNA library (Clontech) using an oligonucleotide containing the unique intrapeptide PCR of mouse T120 and a degenerate oligonucleotide corresponding to rabbit T134. The 392 bp-mouse Ubr1 cDNA fragment was used as a probe for the screening of the Ubr1 cDNA clone from the mouse cDNA library as described below.

iii) cDNA Library Screening, DNA Sequencing, and 5'- and 3'-RACEs.

The λgt11 liver cDNA library (Clontech) was plated on *Escherichia coli* Y1090 (about 3×10$^4$ plaque-forming units/150-mm plate, total 30 plates), and the plaques were lifted onto nylon membrane (Hybond-N, Amersham) and screened by hybridization with the 392 bp-mouse cDNA fragment (obtained from interpeptide PCR) that was labeled with [$^{32}$P]dCTP. The putative positive clones were rescreened until they were plaque-purified. This initial screening using a λgt11 liver cDNA library gave two positive plaques. The purified DNA was digested with EcoRI and then analyzed on 1% agarose gels. Both of the selected positive clones turned out to contain identical 2.45 kb insert by the partial sequencing of the eluted PCR products produced with λDNA and 392 bp-probe specific primers. The cDNA inserts of the two clones were then subcloned into the pBluescript II SK$^+$ plasmid vector, one of them (MR3) was sequenced on both strands. The complete sequencing of MR3 revealed nine regions in deduced amino acid sequence, including the regions of the 392 bp-mouse probe corresponding to T120, T100 and T134, which showed strong identity (62%–100%) to that of the rabbit peptide sequences. The overall identity and similarity of the sum of the nine regions (196 aa) to those of rabbit peptide sequences were 89% and 90%, respectively. This fact indicates that the cloned 2.45 kb insert encodes the mouse homolog of rabbit Ubr1. Furthermore, although the overall homology is relatively low (24% identity and 50% similarity), the deduced amino acid sequence (812 aa from N-terminus) of the cloned 2.45 kb insert showed considerable homology to that (aa 3–960) of *S. cerevisiae* UBR1, further supporting that the cloned 2.45 kb insert encodes the mouse homolog of *S. cerevisiae* UBR1.

The region of similarity began from the ATG codon located between nt 12 and 14 in 2.45 kb sequence, suggesting that this ATG codon may be the start codon in the mouse Ubr1 ORF. There was no stop codon, the poly(A) addition signal or poly(A) tail downstream of the ATG codon, suggesting that the cloned 2.45 kb insert encodes partial N-terminal portion of the mouse Ubr1 ORF considering the observed molecular weight of the purified rabbit Ubr1 (~180 kDa) on SDS-polyacrylamide gel electrophoresis (Reiss and Hershko, *J. Biol. Chem* 265: 3685–3690 (1990)), which is slightly smaller than *S. cerevisiae* UBR1 (225 kDa). Since there was no inframe stop codon upstream of the ATG codon, 5'-RACE PCR (Frohman et al., *Proc. Natl. Acad. Sci. USA* 85: 8998–9002 (1988)) was employed to amplify the upstream region, which contains the inframe stop codon, using an oligonucleotide primer specific for the 2.45 kb clone and a primer complementary to an in vitro-produced 5' oligo(da) tract.

Specifically, 500 ng of poly(A)$^+$ RNA, isolated from mouse L-cells using Oligotex Direct mRNA kit (QIAGEN), was mixed with diethylpyrocarbonate-treated water to make the final volume of 20 µl, incubated at 70° C. for 5 min., and cooled on ice. To this sample were added 20 pmols of a primer corresponding to the antisense strand of the mouse Ubr1 ORF (nt 313–338 in SEQ ID NO:1), 2 µl of 10×PCR buffer (Perkin-Elmer), 2 µl of 0.1 M dithiothreitol (DTT), 1 µl of 10 mM dNTPs, 1 µl of 25 mM MgCl$_2$, and 1 µl of bovine serum albumin (BSA; 2 mg/ml). The sample was incubated at 42° C. for 2 min., followed by the addition of 1 µl of Superscript II reverse transcriptase (Gibco-BRL) and an incubation at 42° C. for another 40 min. The temperature was increased to 55° C., followed by the addition of 1 µl of RNAase H (Gibco-BRL; 2 units/µl) and incubation for 20 min. The resulting cDNA products were purified with QIAquick PCR purification kit (QIAGEN), and were eluted with 50 µl of water. To produce a cDNA-linked 5' oligo(dA) extension, 5 µl of purified cDNA was diluted with 11.5 µl of water, incubated at 70° C. for 5 min., cooled on ice, then mixed with 1 µl of 10×PCR buffer (to the final concentration of 0.5×), 1 µl of 25 mM MgCl$_2$, 0.5 µl of BSA (2 mg/ml), 0.5 µl of 10 mM dCTP, and 0.25 µl of terminal transferase (Boehringer Mannheim). After an incubation at 37° C. for 5 min., the enzyme was inactivated by heating the sample at 65° C. for 10 min. The first round of RACE-PCR amplification was carried out in a 100 µl sample containing 10 µl of 10×PCR buffer, 2.5 mM MgCl$_2$, 5 µl of cDNA linked to oligo(dC), 20 pmols of a primer corresponding to the antisense strand of Ubr1 ORF (nt 306–332 in SEQ ID NO: 1), and 20 pmoles of oligo(dA) anchor primer. The sample was incubated at 94° C. for 5 min., then at 57° C. for 8 min., followed by the addition of AmpliTaq DNA polymerase (Perkin-Elmer) and incubation at 72° C. for 8 min. to produce the complementary cDNA strand. Thereafter, 35 cycles of a 3-step PCR amplification were carried out. Each step involved consecutive incubations for 30 sec at 94° C., 1 min. at 57° C., and 2 min. at 72° C. 2 µl of the first-round PCR product was used for the second-round PCR that utilized, in the same total volume, 0.4 nmols of T-adapter primer (same as the T-anchor primer but lacking T$_{17}$), and 0.4 nmols of a primer corresponding to the antisense strand of Ubr1 ORF (nt 271–293 in SEQ ID No:1). The PCR-produced DNA fragments were inserted into pCR2.1 vector (Invitrogen). Two of the resulting clones gave the 114 bp-upstream sequence of the ATG codon, which contains two successive in-frame stop codons 48 bp and 93 bp upstream of the above ATG codon, suggesting that the putative Met start codon is the likely in vivo start codon of Ubr1 ORF.

Since several lines of evidences (see above and Results) indicated that the cloned 2.45 kb insert encodes partial N-terminal portion of the mouse Ubr1 ORF and since another hybridization screening of the same filters with the cloned 2.45 kb insert as a probe gave no additional positive clones, we employed 3'-RACE to amplify the downstream region of the 2.45 kb insert to use it as a probe for the next cDNA library screening. The 3'-RACE, which was done similarly to 5'-RACE (above) except omitting homopolymer tailing in 3'-RACE, gave 1.3 kb product (corresponding nt 1985–3313 in SEQ ID NO:1) which overlapped with 2.45 kb sequence by 465 bp. Based on the sequence of the 1.3 kb 3'-RACE product, one more 3'-RACE was done and gave 1.2 kb (corresponding nt 3039–3835 in mouse Ubr1 cDNA sequence), in which 797 bp Ubr1 cDNA sequence was fused with the 3'-UTR region of mouse glutathione S-transferase (GST) mRNA, which seems to be an artifact.

To get full length cDNA, λgt10 cDNA library (Clontech) from MEL-C19 cells was plated on *Escherichia coli* C600Hfl, hybridized with a labeled 998 bp-probe (nt 2470–3467 SEQ ID NO:1) synthesized by PCR on the basis of the sequence from 3'-RACE. By PCR analysis of the positive plaque lysates (or phage λDNA) followed by partial sequencing, the insert size and relative location of each of fourteen independent positive clones ranging in size from 0.6 to 4.6 kb were determined. Among them, five clones which overlap each other and cover the full length cDNA were subcloned into Bluescript II SK$^+$ (MR16 with size of 3.0 kb, MR17 with size of 2.8 kb, MR19 with size of 2.2 kb, MR20 with size of 1.4 kb, and MR23 with size of 4.6 kb) and sequenced on both strands. Especially in the ORF region, at least two independent clones (from cDNA library screening, 5'- or 3'-RACE) were sequenced. Among them, MR16 contained the putative ATG start codon of the initial clone (2.45 kb, see above) preceded by 57 bp-mouse Ubr1 5'-UTR containing an inframe stop codon 48 bp upstream of the ATG codon. The 57 bp-5'-UTR region of MR16 was preceded by 360 bp mouse 18S ribosomal RNA sequence (EMBL accession number X00686), which is thought to be an artifact during library construction. MR19 contained an ORF showing considerable homology to yeast UBR1 followed by a stop codon preceding a poly(A) addition signal 41 bp downstream which was followed by poly($A_{21}$) tail 9 bp downstream, suggesting that MR19 contains Ubr1 C-terminal region and 3'-UTR. MR20 overlapped with 3'-region of MR16 and 5'-region of MR19, suggesting that MR16, MR20 and MR19 covers the full length ORF of mouse Ubr1 cDNA and also 3'- and 5'-UTR regions. These three clones (MR16, MR20 and MR19) were joined into a single contiguous fragment to make MR26 which contains 57 bp-5'UTR, 5271 bp Ubr1 ORF (1757 residues) and 58 bp-3'-UTR. Specifically, the 1.2 kb-EcoRI-XbaI fragment of MR20 was subcloned into pBluescript II $SK^+$ to yield MR24. Subsequently, the 2.2 kb-XbaI fragment of MR19 was subcloned into MR24 to make MR25. Then the 3 kb-MscI-NotI fragment of MR25 was inserted into MR16 to make MR26 which contains the full length mouse Ubr1 ORF shown in SEQ ID NO:1.

iv) Cloning of Partial Human UBR1 cDNA fragment (1 kb) using RT-PCR.

Poly$(A)^+$ RNA was isolated from human 293 cells using Oligotex Direct mRNA kit (QIAGEN). The first-strand cDNA was synthesized from 500 ng of Poly$(A)^+$ RNA using oligo(dT) priming and Superscript II reverse transcriptase (Gibco-BRL), followed by treatment of 2 units of RNAase H (Gibco-BRL) and purified with QIAquick PCR purification kit (QIAGEN). 30 ng of the synthesized cDNA was used for PCR using AmpliTaq DNA polymerase (Perkin-Elmer) and several different primers sets corresponding to mouse Ubr1 cDNA sequence. One of the reactions gave the 1 kb product which was subcloned into pCR2.1 vector (Invitrogen) and sequenced. The sequence of the partial human UBR1 cDNA fragment is shown in SEQ ID NO:2.

v) Cloning of Partial Human UBR1 Genomic DNA Fragments using Genomic PCR.

The human genomic DNA was isolated from human 293 cells by conventional method and was used for PCR using Expand High Fidelity PCR System (Boehringer Mannheim) and exon specific primers. The PCR products were subcloned into pCR2.1 vector (Invitrogen) to give HR8 (insert size 6.3 kb), HR6-4 (insert size 5.8 kb), HR2-25 (insert size 3.6 kb), HR7-2 (insert size 5.4 kb). The four inserts described above were analyzed by partial DNA sequencing and were shown to cover ~21 kb of the human UBR1 gene with overlapping of 100–150 bp. The exon/intron junctions were determined by partial sequencing.

vi) Northern and Southern Hybridizations.

Mouse and human multiple tissue Northern blots with 2 μg of poly$(A)^+$ RNA per lane (Clontech), isolated from various adult mouse or human tissues, were hybridized with the $p^{32}$-labeled probes (1 kb-human UBR1 cDNA fragment for human blot and 2 kb and 648 bp mouse Ubr1 cDNA fragments corresponding to nt 116–2124 and nt 4738–5385, respectively, in mouse Ubr1 cDNA sequence (SEQ ID NO: 1) eluted from the gel after PCR. Hybridization was carried out as suggested in the manufacturer's protocol. The intactness of the RNA samples on the blots were checked with the β-actin probe provided with them. For Southern blot analysis genomic DNAs, isolated by conventional method from mouse L-cell and human 293 cell and digested with various restriction enzymes, were hybridized with 1228 bp or 1169 bp mouse Ubr1 cDNA probes for mouse blot (corresponding to nt 105–1332 and nt 610–1778, of SEQ ID NO: 1, respectively) or 1 kb human UBR1 cDNA probes for human blot under either high stringency (final washing; 0.1×SSC/ 0.1% SDS at 55° C.) or low stringency conditions (final washing; 0.2×SSC/0.1% SDS at 42° C.).

vii) Interspecific Mouse Backcross Mapping.

The chromosomal position of mouse Ubr1 was determined using the interspecific backcross analysis. Interspecific backcross progeny were generated by mating (C57BL/ 6J×M. spretus) $F_1$ females and C57BL/6J males as described (Copeland and Jenkins, Trends Genet. 7: 113–118 (1991)). A total of 205 $N_2$ mice were used to map the Ubr1 locus (see text for details). DNA isolation, restriction enzyme digestion, agarose gel electrophoresis, Southern blot transfer and hybridization were performed essentially as described (Jenkins et al., J. Virol. 43: 26–36 (1982)). All blots were prepared with Hybond-$N^+$ nylon membrane (Amersham). A 1169 bp-fragment of mouse cDNA corresponding to nt 610–1778, was labeled with [$\alpha^{32}P$] dCTP using a random primed labeling kit (Stratagene); washing was done to a final stringency of 1.0×SSC, 0.1% SDS, 65° C. Fragments of 5.6, 5.4, and 4.3 kb were detected in ScaI digested C57BL/6J DNA and a fragment of 15.0 kb was detected in ScaI digested M. spretus DNA. The presence or absence of the 15.0 kb ScaI M. spretus-specific fragment was followed in backcross mice. A description of the probes and RFLPs for the loci linked to Ubr1 including Thbs1 and B2m has been reported previously (Lawler et al., Genomics 11: 587–600 (1991)). One locus has not been reported previously for this interspecific backcross. The probe for erythrocyte protein band 4.2 (Epb4.2) was an ~800 bp EcoRI fragment of human cDNA that detected a 7.8 kb SphI fragment in C57BL/6J DNA and a 14.0 kb SphI fragment in M. spretus DNA. Recombination distances were calculated using Map Manager, version 2.6.5. Gene order was determined by minimizing the number of recombination events required to explain the allele distribution patterns.

vii) Human chromosome mapping.

Fluorescence in situ hybridization (FISH) was performed on human chromosomes prepared from synchronized cultures of lymphocytes isolated from cord blood (Heng et al, Proc. Natl. Acad. Sci. USA 89: 9509–9513 (1992)). Human chromosomes were probed with mixture of plasmids (HR8, HR6-4, HR2-25, and HR7-2) containing human UBR1 genomic DNA fragments (~21 kb) corresponding to partial human UBR1 cDNA fragment (1 kb, nt 2540–3532 in SEQ ID NO: 1). Probes were labeled with biotinylated DATP using the BRL BioNick labeling kit (15° C., 1 hr), hybridized to the chromosome spreads, and detected with FITC-avidin. Signals were amplified by incubation with biotinylated goat anti-avidin followed by a second round of incubation with FITC-avidin. Chromosome banding patterns were obtained with the chromatin-binding fluorescent dye 4'-6-diamino-2-phenylindole (DAPI). Chromosomal localization of human UBR1 was made by superimposing photographs of the hybridization signals with photographs of the DAPI banding patterns.

Results i) Peptide sequencing and PCR cloning.

The fourteen peptide sequences of the purified rabbit Ubr1 protein showed no significant homology to any of the proteins deposited in the database, even to *S. cerevisiae* UBR1 protein, a counterpart of rabbit Ubr1 protein. A second independent purification of rabbit Ubr1 protein from reticulocyte lysates using similar method with that of the first approach (Reiss and Hershko, *J. Biol. Chem* 265: 3685–3690 (1990)) followed by determination of tryptic peptide sequences was done and gave three peptide sequences (PEP1, PEP2 and PEP3) which are identical to those of the first approach, supporting that the purified protein and the determined sequences are authentic.

On the basis of the peptide sequences, an initial attempt was made to obtain the unique sequence (not degenerate) of rabbit Ubr1 cDNA using degenerate oligonucleotide primers and intrapeptide PCR, which amplify the internal region of a peptide sequence (FIG. 1 and see Materials and Methods). Unique sequences were determined from intrapeptide PCR and corresponded to regions of sequence encoding several of the 14 rabbit peptide sequences (e.g., T122, T120 and PEP2). The intrapeptide PCR of T120 from mouse λgt11 liver cDNA gave a unique sequence encoding the same amino acids (with third codon redundancies) with that from rabbit genomic DNA of T120. The unique sequence of PEP1 was variable (four different types in 8 clones). The reason for this variable unique sequences is unclear. Subsequently, the oligonucleotide PCR primers, bearing the unique sequence from intrapeptide PCR, together with the original degenerate PCR primers were used for the amplification of rabbit Ubr1 cDNA fragment between the peptide sequences from rabbit liver cDNA library (interpeptide PCR) (FIG. 1). One of the interpeptide PCRs yielded a 392 bp-PCR product bearing T120 and T134 on both ends, and also internally bearing T100, indicating it to be authentic rabbit Ubr1 cDNA fragment corresponding to the purified protein. A 392 bp-mouse Ubr1 cDNA fragment corresponding to the 392 bp-rabbit UBR1 cDNA fragment was also obtained from the mouse cDNA library (see Materials and Methods). Sequencing of the 392 bp-mouse Ubr1 cDNA fragment revealed three regions corresponding to T120, T100 and T134 peptide sequences of 392 bp-rabbit Ubr1 cDNA fragment. The 392 bp-rabbit and mouse Ubr1 cDNA fragments shared 88% and 89% identity in nucleotide and protein sequence, respectively. They showed no significant homology to any sequence in data base including *S. cerevisiae* UBR1.

ii) Isolation of mouse Ubr1 cDNA.

In the initial cDNA screening using the 392 bp-mouse cDNA fragment and subsequent screening using a probe based on the 3-RACEs gave several positive clones ranging in size from 0.6 to 4.6 kb. Among them, MR16 with size of 3.0 kb containing the ATG start codon preceded by 57 bp-5'-UTR with an in-frame stop codon 48 bp upstream of the ATG start codon, MR20 with size of 1.4 kb containing the middle region of the Ubr1 ORF, and MR19 with size of 2.2 kb containing the C-terminal region of the Ubr1 ORF and 58 bp-3'-UTR covered the full length cDNA ORF. The comparison of the partial sequence of MR23 (4.6 kb insert) with other clones (MR3, MR16, MR20, and MR19) and its sequence search revealed that it contains the C-terminal half of Ubr1 ORF (from aa 2703) flanked in 5'-region by the polyprotein sequence of Friend murine leukemia virus with the orientation reversed, which is believed to be a result from an artifact. Furthermore, the Ubr1 ORF of MR23 was followed by a long 3'-UTR (1010 bp), in which the poly(A) addition site in MR19 was bypassed, the significance of which is unclear.

The resulting mouse Ubr1 cDNA ORF was composed of 5271 bp encoding a 1757-residues (200 kDa) protein, which is largely similar to that (225 kDa) of *S. cerevisiae* UBR1 and the observed molecular weight (180 kDa) of rabbit Ubr1, purified from reticulocyte lysate, on SDS-PAGE (Reiss and Hershko, *J. Biol. Chem* 265: 3685–3690 (1990)). The upstream sequence of the putative (first) ATG start codon, preceded by two in-frame stop codons 48 bp and 93 bp upstream, was largely in an agreement with Kozak's rules (Kozak, M., *J. Biol. Chem.* 266: 19867–19870 (1991)) in that A in position −3 and G in position +4. Immediately downstream of the first ATG codon there are two more ATG codons. Both the second and third ATG codons (the 6th and 12th amino acids in the ORF) have a purine (G and A, respectively) in −3 position and G in +4 position, indication them to be potential alternative start codons. One prominent feature of the N-terminus of the ORF is that among the first 13 residues in ORF 7 are charged (6 negative and 1 positive) amino acids. The meaning of the second and third ATG codons and the highly charged (negative) N-terminal 13 residues are unclear.

iii) Deduced amino acid sequence of mouse Ubr1.

Although mouse Ubr1 protein sequence showed relatively low overall homology to *S. cerevisiae* UBR1 (22% identity and 48% similarity) (for *S. cerevisiae* UBR1 sequence see GenBank Accession No. P19812), certain subdomains showed significant homology. More specifically, six specific regions of homology were identified indicating functional relationship of the two proteins. These regions were arbitrarily designated Regions I–VI with designations assigned in order based on location from N- terminus to C- terminus (i.e., Region I is the most C-terminal of the VI regions of homology). Furthermore, comparison of mouse Ubr1 sequence with those available in sequence databases using BLAST programs (Altschul et al., *J. Mol. Biol.* 215: 403–410 (1990)) through the National Center for Biotechnology Information revealed several proteins showing significant homology; a 1927 aa-*Caenorhabditis elegans* ORF (GenBank Accession number U88308) (32% identity and 53% similarity; termed *C. elegans* Ubr1[2]), a 1872 aa-*S. cerevisiae* ORF (GenBank Accession number Z73196) (21% identity and 47% similarity; termed *S. cerevisiae* UBR2), a 2168aa-*C. elegans* ORF (GenBank Accession number U40029) (21% identity and 45% similarity; termed *C. elegans* Ubr2) and a 794 aa-*Arabidopsis thaliana* CER3 (eceriferum 3; 26% identity and 49% similarity). Besides these proteins, a 147 aa-partial ORF of *Candida albicans* corresponding to the region near N-terminus of mouse Ubr1, and a 272 aa-partial ORF of *Schizosaccharomyces pombe* corresponding to the region near C-terminus of mouse Ubr1 (GenBank Accession number M26699; termed *S. pombe* UBR2) also showed significant homologies to the members of UBR1 family. Although the overall homology in these proteins are relatively low (17–32% identity), alignment of their protein sequences revealed several distinctive regions, suggesting that mouse Ubr1 and yeast UBR1, together with their related proteins of previously unknown function, belong to a distinct UBR1 family. The recognition of this fact was made possible exclusively by the isolation and identification of the mouse and human Ubr1 sequences as disclosed herein.

One of the prominent regions of UBR1 proteins is a 66 aa-region (Region I) near N-terminus (in mouse Ubr1), which shows the highest homology among all the regions (61% identity and 75% similarity between mouse Ubr1 and *C. elegans* Ubr1). This region contains a distinctive Cys/His rich domain which does not fit to any other known Cys/His rich motifs. This Cys/His domain is conserved in all the UBR1 family members including mouse Ubr1, *C. elegans* Ubr1, *S. cerevisiae* UBR1, *S. cerevisiae* UBR2, *C. elegans*

Ubr2 and a partial N-terminal ORF of *Candida albicans* ORF (http://alces.med.umn.edu/bin/genelist?LUBR1) (termed *C. albicans* UBR1), except *Arabidopsis thaliana* CER3 which contains only Region V and VI. Although this Cys/His structure is likely to be a zinc finger, the number and spacing of Cys and His residues in this structure did not fit to any other known zinc finger. Region V also contains a distinctive Cys/His domain which is conserved in all the UBR1 family members. By comparison of this Cys/His domain with the already known Cys/His structures, the Cys/His domain in Region V was turned out to belong to a RING-H2 finger, a subfamily RING fingers (Borden and Freemont, *Curr Opin Struct Biol* 6: 395–401 (1996)). Several known examples of RING-H2 finger-containing proteins are PSMP, CELG, FAR1, PEP3 and PEP5 (for references of each sequence, see Freemont, P. S., *Ann. NY Acad. Sci.* 684: 174–192 (1993)). One distinctive feature of the RING-H2 of UBR1 family is that the length of loop1 (53 aa–85 aa) is longer than that (12aa–35aa) of those known RING-H2 finger proteins. Other extensive homologies between UBR1 proteins are observed in the 115-aa Region VI (in mouse Ubr1) near C-terminus (24%–50% identity and 46–70% similarity to Region VI of mouse Ubr1). Region VI of *C. elegans* Ubr1 showed highest homology (50% identity and 70% similarity) to that of mouse Ubr1. However, the region VI of *S. cerevisiae* UBR1, the homolog of mouse Ubr1, showed the lowest homology (24% identity and 46% similarity) among UBR1 family members including *S. cerevisiae* UBR2, *C. elegans* Ubr2, *A. thaliana* CER3 and *S. pombe* UBR2. Furthermore, while region VI of all the other related proteins was located 4–14aa from C-terminus of each protein, *S. cerevisiae* UBR1 had an additional 132 and 159 residue-tail which is highly rich in (mainly negative) charged residues (36% and 33%). The significance of the tails is unclear. Region IV also shows high homology in all the UBR1 family members except *C. elegans* UBR2. No protein showed considerable homology to this region when searched using BLAST.

iv) Cloning of Partial Human cDNA and Genomic DNA.

To obtain probes for chromosome mapping of human UBR1, a partial human UBR1 cDNA (1 kb), corresponding nt 2218–3227 of mouse Ubr1 cDNA sequence, was cloned by RT-PCR using Poly(A)$^+$ RNA isolated from human 293 cells. The nucleotide and deduced amino acid sequences shared 90% and 93% identities, respectively, with mouse Ubr1 cDNA sequence. Partial human UBR1 genomic DNA fragments (HR8, HR6-4, HR2-25 and HR7-2 with insert sizes of 6.3 kb, 5.8 kb, 3.6 kb and 5.4 kb, respectively, with overlapping of 100–150 bp), corresponding to 1 kb cDNA and ~21 kb genomic DNA, were cloned by genomic PCR using genomic DNA from human 293 cells as a template and the primers based on the human UBR1 cDNA sequence. Partial DNA sequencing of the cloned genomic DNA fragments showed that the ~21 kb genomic DNA region was composed of 11 exons ranging in length from 49 bp to 155 bp. All of the exon/intron junctions contained the consensus GT and AG dinucleotides characteristic of mammalian nuclear pre-mRNA splice sites (Shapiro and Senapathy, *Nucleic Acids Res.* 15: 7155–7174 (1987)).

v) Northern and Southern blot hybridizations of mouse Ubr1 and human UBR1.

The expression of mouse Ubr1 and human UBR1 was tested by Northern blot analysis using 2 kb (N-terminal region) or 640 bp (C-terminal region) mouse Ubr1 cDNA fragments for mouse blot and 1 kb-human UBR1 cDNA fragment for human blot. A poly A$^+$ transcript of ~8.0 kb was ubiquitously detected in different mouse tissues using either of the probes (N- or C-terminal region), with relatively high level in skeletal muscle, heart and brain and with lowest level in kidney. The testis-derived Ubr1 mRNA existed as two species: the minor one comigrated with the ~8.0 kb Ubr1 mRNA of the other tissues, while the major one had the apparent size of ~6 kb, which is similar to Northern blot of testis-derived Ntan1 mRNA in which the minor one comigrated with the ~1.4 kb Ntan1 mRNA of the other tissues, while the major one had the apparent size of ~1.1 kb (Grigoryev et al., *J. Biol. Chem.* 271: 28521–28532 (1996)). It is unclear whether the testis specific Ubr1 and Ntan1 Northern patterns were the result of RNA degradation during isolation, specific cleavage of RNA, or two distinct primary transcripts (from different poly(A) addition site or alternative splicing), like $E2_{14K}$ mRNA. The mouse $E2_{14K}$, the mouse homologs of *S. cerevisiae* UBC2 which is a component of the yeast N-end rule, also shows the highest mRNA expression level in skeletal (Grigoryev et al., *J. Biol. Chem.* 271: 28521–28532 (1996)). The upstream region of the rabbit $E2_{14K}$ ORF contains several putative binding sites for MyoD, a muscle-specific transcription factor (Weintraub) et al., *Genes Devel.* 5: 1377–1386 (1991)). The human UBR1 mRNA showed similar Northern blot pattern with that of mouse Ubr1.

Southern blotting analysis of mouse or human genomic DNA has revealed rather simple band patterns under either high (final washing; 0.1×SSC/0.1% SDS at 55° C.) or low stringency conditions (final washing; 0.2×SSC/0.1% SDS at 42° C.), suggesting the presence of a single copy of Ubr1 gene in genome and the absence of genes whose structures are closely related to Ubr1 at nucleotide level. However, we cannot exclude the presence of mammalian E3(s) closely related with Ubr1 only at amino acid level. Indeed, several lines of evidences indicate the presence of E3β in rabbit reticulocyte lysates which is believed to be another mammalian ubiquitin-protein ligase recognizing small uncharged N-termini (Ala, Ser, Thr: type III N-terminal destabilizing residues) of the N-end rule (Gonda et al., *J. Biol. Chem.* 264: 16700–16712 (1989)). Although they have different substrate specificities, rabbit Ubr1 and E3β share several properties (Hershko and Ciechanover, *Annu. Rev. Biochem.* 61: 761–807 (1992)). Therefore, it is likely that the sequences of these two proteins are similar.

vi) Interspecific Mouse Backcross Mapping.

The mouse chromosomal location of Ubr1 was determined by interspecific backcross analysis using progeny derived from matings of [(C57BL/6J×*Mus spretus*)F$_1$× C57BL/6J] mice. This interspecific backcross mapping panel has been typed for over 2400 loci that are well distributed among all the autosomes as well as the X chromosome (Copeland and Jenkins, *Trends Genet.* 7: 113–118 (1991)). C57BL/6J and *M. spretus* DNAs were digested with several enzymes and analyzed by Southern blot hybridization for informative restriction fragment length polymorphisms (RFLPs) using a mouse cDNA Ubr1 probe. The 15.0 kb ScaI *M. spretus* RFLP (see Materials and Methods) was used to follow the segregation of the Ubr1 locus in backcross mice. The mapping results indicated that Ubr1 is located in the central region of mouse chromosome 2 linked to Thbs1, Epb4.2, and B2m. Although 66 mice were analyzed for every marker and are shown in the segregation analysis, up to 133 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere—

Thbs1—4/133—Ubr1—0/113—Epb4.2—1/122—B2m. The recombination frequencies (expressed as genetic distances in centiMorgans (cM) ± the standard error) are— Thbs1—3.0+/−1.5—[Ubr1, Epb4.2]—0.8+/−0.8—B2m. No recombinants were detected between Ubr1 and Epb4.2 in 113 animals typed in common suggesting that the two loci are within 2.7 cM of each other (upper 95% confidence limit).

The interspecific map of chromosome 2 was compared with a composite mouse linkage map that reports the map location of many uncloned mouse mutations (provided from Mouse Genome Database, a computerized database maintained at The Jackson Laboratory, Bar Harbor, Me.). Ubr1 mapped in a region of the composite map that lacks mouse mutations with a phenotype that might be expected for an alteration in this locus. The central region of mouse chromosome 2 shares a region of homology with human chromosome 15q. The placement of Ubr1 in this interval in mouse suggests that human homolog will map to 15q, as well.

vii) Chromosomal localization of the human UBR1 locus.

The chromosome localization of mouse Ubr1 was independently confirmed and refined by chromosome mapping of human UBR1 by FISH using human UBR1 genomic clones (HR8, HR6-4, HR2-25 and HR7-2) as the hybridization probes. Under the conditions described in Materials and Methods, the hybridization efficiency was approximately 91% for these probes (among 100 checked mitotic figures, 91 of them showed signals on one pair of the chromosomes). Since the DAPI banding was used to identify the specific chromosome, the assignment between signal from probes and the long arm of chromosome 15 was obtained. The detailed position was further determined based on the summary from 10 photos. There was no additional locus picked by FISH detection under the condition used, therefore, UBR1 is located at human chromosome 15q15–15q21.1, which is in a good agreement with the result of mouse chromosome mapping of Ubr1.

What is claimed is:

1. A method for inhibiting the N-end rule pathway in a mammalian cell comprising inhibiting the expression of the Ubr1 gene in the mammalian cell.

2. The method of claim 1 wherein expression is inhibited by contacting mRNA encoding the Ubr1 gene with an inhibitory molecule which specifically hybridizes to the Ubr1 mRNA under physiological conditions thereby inhibiting the translation of the Ubr1 mRNA.

3. The method of claim 2 wherein the inhibitory molecule hybridizes specifically with the nucleic acid sequence of SEQ ID NO 1 under stringent hybridization conditions.

4. The method of claim 2 wherein the inhibitory molecule hybridizes specifically with the nucleic acid sequence of SEQ ID NO 2 under stringent hybridization conditions.

5. The method of claim 1 wherein the mammalian cell is infected with an intracellular pathogen.

6. The method of claim 5 wherein expression is inhibited by contacting mRNA encoding the Ubr1 gene with an inhibitory molecule which specifically hybridizes to the Ubr1 mRNA under physiological conditions thereby inhibiting the translation of the Ubr1 mRNA.

7. The method of claim 6 wherein the inhibitory molecule hybridizes specifically with the nucleic acid sequence of SEQ ID NO 1 under stringent hybridization conditions.

8. The method of claim 6 wherein the inhibitory molecule hybridizes specifically with the nucleic acid sequence of SEQ ID NO 2 under stringent hybridization conditions.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 6395 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..5385

(xi) SEQUENCE DESCRIPTION: SEQ ID NO:1:

```
CCTGACTTTC AGGGGCCGTC GTAAAAGTGT CGTCCCTGTC GCGTCGGGCC GGCCACAGGT        60

TTCCGCTAGC TGGCGGCCGG GGGTCGGGAA CTGCGGGCGT TCGTTTCCCT TAAG ATG         117
                                                             Met
                                                              1

GCG GAC GAA GAG ATG GAC GGC GCC GAG AGG ATG GAC GTC AGC CCG GAG        165
Ala Asp Glu Glu Met Asp Gly Ala Glu Arg Met Asp Val Ser Pro Glu
              5                  10                  15

CCT CCC CTG GCC CCG CAG CGG CCG GCA TCG TGG TGG GAT CAG CAA GTT        213
Pro Pro Leu Ala Pro Gln Arg Pro Ala Ser Trp Trp Asp Gln Gln Val
         20                  25                  30

GAT TTC TAT ACT GCT TTC TTA CAT CAT TTG GCA CAA TTA GTG CCA GAA        261
Asp Phe Tyr Thr Ala Phe Leu His His Leu Ala Gln Leu Val Pro Glu
     35                  40                  45

ATT TAT TTT GCT GAG ATG GAC CCA GAT TTG GAA AAG CAA GAA GAG AGT        309
Ile Tyr Phe Ala Glu Met Asp Pro Asp Leu Glu Lys Gln Glu Glu Ser
 50                  55                  60                  65

GTA CAG ATG TCA ATA CTC ACT CCT TTG GAG TGG TAC TTA TTT GGA GAG        357
Val Gln Met Ser Ile Leu Thr Pro Leu Glu Trp Tyr Leu Phe Gly Glu
                 70                  75                  80

GAT CCG GAT ATT TGC TTA GAG AAA TTA AAA CAC AGT GGA GCG TTC CAG        405
Asp Pro Asp Ile Cys Leu Glu Lys Leu Lys His Ser Gly Ala Phe Gln
             85                  90                  95
```

-continued

```
TTG TGT GGG AAG GTT TTC AAA AGT GGA GAA ACA ACA TAT TCC TGT AGG       453
Leu Cys Gly Lys Val Phe Lys Ser Gly Glu Thr Thr Tyr Ser Cys Arg
            100                 105                 110

GAT TGT GCA ATT GAT CCA ACG TGT GTG CTC TGT ATG GAC TGC TTC CAA       501
Asp Cys Ala Ile Asp Pro Thr Cys Val Leu Cys Met Asp Cys Phe Gln
            115                 120                 125

AGT AGT GTT CAT AAA AAC CAT CGT TAC AAG ATG CAT ACT TCT ACT GGA       549
Ser Ser Val His Lys Asn His Arg Tyr Lys Met His Thr Ser Thr Gly
130                 135                 140                 145

GGG GGC TTC TGT GAC TGT GGA GAC ACA GAA GCG TGG AAA ACT GGC CCT       597
Gly Gly Phe Cys Asp Cys Gly Asp Thr Glu Ala Trp Lys Thr Gly Pro
                150                 155                 160

TTT TGT GTG GAT CAC GAG CCT GGA AGA GCA GGT ACT ACA AAA GAG AGC       645
Phe Cys Val Asp His Glu Pro Gly Arg Ala Gly Thr Thr Lys Glu Ser
                165                 170                 175

TTA CAT TGC CCA TTG AAT GAA GAG GTG ATT GCT CAA GCC AGG AGA ATA       693
Leu His Cys Pro Leu Asn Glu Glu Val Ile Ala Gln Ala Arg Arg Ile
                180                 185                 190

TTC CCT TCG GTG ATA AAA TAC ATT GTA GAA ATG ACT ATA TGG GAA GAA       741
Phe Pro Ser Val Ile Lys Tyr Ile Val Glu Met Thr Ile Trp Glu Glu
            195                 200                 205

GAA AAG GAA TTG CCT CCT GAA CTG CAG ATA AGG GAG AAA AAT GAA CGA       789
Glu Lys Glu Leu Pro Pro Glu Leu Gln Ile Arg Glu Lys Asn Glu Arg
210                 215                 220                 225

TAC TAT TGT GTC CTT TTC AAC GAT GAG CAC CAT TCG TAT GAT CAT GTG       837
Tyr Tyr Cys Val Leu Phe Asn Asp Glu His His Ser Tyr Asp His Val
                230                 235                 240

ATC TAC AGT CTG CAG AGA GCT CTA GAT TGC GAG CTT GCA GAG GCA CAG       885
Ile Tyr Ser Leu Gln Arg Ala Leu Asp Cys Glu Leu Ala Glu Ala Gln
                245                 250                 255

CTG CAC ACG ACT GCC ATC GAC AAA GAG GGT CGC CGG GCT GTC AAA GCA       933
Leu His Thr Thr Ala Ile Asp Lys Glu Gly Arg Arg Ala Val Lys Ala
                260                 265                 270

GGT GTG TAT GCC ACT TGC CAG GAA GCA AAG GAG GAT ATA AAG AGT CAC       981
Gly Val Tyr Ala Thr Cys Gln Glu Ala Lys Glu Asp Ile Lys Ser His
            275                 280                 285

TCA GAG AAC GTC TCT CAG CAC CCC CTC CAT GTG GAA GTG CTG CAC TCC      1029
Ser Glu Asn Val Ser Gln His Pro Leu His Val Glu Val Leu His Ser
290                 295                 300                 305

GTG GTT ATG GCT CAC CAG AAA TTC GCT CTG CGC CTT GGC TCC TGG ATG      1077
Val Val Met Ala His Gln Lys Phe Ala Leu Arg Leu Gly Ser Trp Met
                310                 315                 320

AAC AAA ATT ATG AGC TAT TCA AGT GAC TTT AGA CAG ATA TTT TGC CAG      1125
Asn Lys Ile Met Ser Tyr Ser Ser Asp Phe Arg Gln Ile Phe Cys Gln
                325                 330                 335

GCC TGC CTC GTA GAA GAA CCT GGC TCT GAA AAT CCC TGT CTT ATA AGC      1173
Ala Cys Leu Val Glu Glu Pro Gly Ser Glu Asn Pro Cys Leu Ile Ser
            340                 345                 350

AGA CTA ATG CTT TGG GAT GCA AAA CTT TAT AAA GGT GCC CGT AAG ATC      1221
Arg Leu Met Leu Trp Asp Ala Lys Leu Tyr Lys Gly Ala Arg Lys Ile
    355                 360                 365

CTT CAT GAA TTG ATC TTT AGT AGT TTT TTT ATG GAG ATG GAA TAC AAA      1269
Leu His Glu Leu Ile Phe Ser Ser Phe Phe Met Glu Met Glu Tyr Lys
370                 375                 380                 385

AAA CTC TTT GCT ATG GAA TTT GTG AAG TAT TAT AAA CAA CTG CAG AAA      1317
Lys Leu Phe Ala Met Glu Phe Val Lys Tyr Tyr Lys Gln Leu Gln Lys
                390                 395                 400

GAG TAC ATC AGC GAC GAC CAC GAG AGA AGC ATC TCC ATA ACC GCC CTG      1365
Glu Tyr Ile Ser Asp Asp His Glu Arg Ser Ile Ser Ile Thr Ala Leu
```

-continued

```
                    405                     410                     415
TCC GTG CAG ATG CTC ACC GTC CCG ACC TTG GCC CGG CAT CTT ATT GAA          1413
Ser Val Gln Met Leu Thr Val Pro Thr Leu Ala Arg His Leu Ile Glu
            420                     425                 430

GAG CAG AAT GTT ATT TCT GTC ATT ACT GAA ACG CTG CTA GAA GTT TTA          1461
Glu Gln Asn Val Ile Ser Val Ile Thr Glu Thr Leu Leu Glu Val Leu
        435                     440                 445

CCT GAA TAC TTG GAC AGG AAC AAT AAA TTC AAC TTC CAG GGT TAT AGC          1509
Pro Glu Tyr Leu Asp Arg Asn Asn Lys Phe Asn Phe Gln Gly Tyr Ser
450                     455                     460                 465

CAG GAC AAA CTG GGA AGA GTC TAC GCA GTT ATA TGT GAC CTA AAG TAT          1557
Gln Asp Lys Leu Gly Arg Val Tyr Ala Val Ile Cys Asp Leu Lys Tyr
            470                     475                 480

ATC CTG ATT AGC AAG CCT GTC ATA TGG ACA GAA CGA TTA AGA GCG CAG          1605
Ile Leu Ile Ser Lys Pro Val Ile Trp Thr Glu Arg Leu Arg Ala Gln
            485                     490                 495

TTC CTG GAA GGT TTC CGG TCT TTT CTG AAG ATT CTT ACC TGT ATG CAG          1653
Phe Leu Glu Gly Phe Arg Ser Phe Leu Lys Ile Leu Thr Cys Met Gln
        500                     505                 510

GGA ATG GAA GAA ATC AGA AGA CAA GTT GGA CAA CAC ATT GAA GTG GAC          1701
Gly Met Glu Glu Ile Arg Arg Gln Val Gly Gln His Ile Glu Val Asp
        515                     520                 525

CCT GAC TGG GAG GCT GCC ATC GCT ATA CAG ATG CAA CTA AAG AAT ATT          1749
Pro Asp Trp Glu Ala Ala Ile Ala Ile Gln Met Gln Leu Lys Asn Ile
530                     535                     540                 545

TTG CTC ATG TTC CAA GAG TGG TGT GCT TGT GAT GAA GAT CTC TTA CTG          1797
Leu Leu Met Phe Gln Glu Trp Cys Ala Cys Asp Glu Asp Leu Leu Leu
                550                     555                 560

GTG GCT TAT AAA GAA TGT CAC AAA GCT GTA ATG AGG TGC AGT ACA AAT          1845
Val Ala Tyr Lys Glu Cys His Lys Ala Val Met Arg Cys Ser Thr Asn
            565                     570                 575

TTC ATG TCC AGT ACC AAG ACA GTA GTG CAA TTG TGC GGT CAT AGT CTG          1893
Phe Met Ser Ser Thr Lys Thr Val Val Gln Leu Cys Gly His Ser Leu
        580                     585                 590

GAA ACC AAA TCC TAC AAA GTG TCT GAG GAC CTT GTA AGC ATA CAC CTG          1941
Glu Thr Lys Ser Tyr Lys Val Ser Glu Asp Leu Val Ser Ile His Leu
        595                     600                 605

CCA CTC TCT AGA ACA CTT GCT GGT CTT CAT GTA CGT TTA AGC AGA CTA          1989
Pro Leu Ser Arg Thr Leu Ala Gly Leu His Val Arg Leu Ser Arg Leu
610                     615                     620                 625

GGT GCT ATT TCA AGA CTG CAT GAA TTT GTG CCT TTT GAC AGC TTT CAA          2037
Gly Ala Ile Ser Arg Leu His Glu Phe Val Pro Phe Asp Ser Phe Gln
                630                     635                 640

GTA GAG GTC CTG GTG GAG TAC CCG CTG CGC TGC CTG GTC CTG GTG GCT          2085
Val Glu Val Leu Val Glu Tyr Pro Leu Arg Cys Leu Val Leu Val Ala
            645                     650                 655

CAG GTT GTT GCT GAG ATG TGG CGA AGA AAC GGG CTC TCA CTC ATC AGC          2133
Gln Val Val Ala Glu Met Trp Arg Arg Asn Gly Leu Ser Leu Ile Ser
            660                     665                 670

CAG GTT TTC TAT TAT CAA GAT GTT AAA TGC AGG GAG AAA ATG TAC GAT          2181
Gln Val Phe Tyr Tyr Gln Asp Val Lys Cys Arg Glu Glu Met Tyr Asp
        675                     680                 685

AAA GAT ATC ATC ATG CTT CAG ATT GGA GCA TCT ATA ATG GAT CCC AAC          2229
Lys Asp Ile Ile Met Leu Gln Ile Gly Ala Ser Ile Met Asp Pro Asn
690                     695                     700                 705

AAG TTC TTG TTA CTG GTA CTT CAG AGA TAT GAA CTT ACT GAT GCT TTT          2277
Lys Phe Leu Leu Leu Val Leu Gln Arg Tyr Glu Leu Thr Asp Ala Phe
                710                     715                 720

AAC AAG ACC ATA TCC ACA AAA GAC CAG GAT TTG ATT AAA CAG TAT AAT          2325
```

-continued

```
                Asn Lys Thr Ile Ser Thr Lys Asp Gln Asp Leu Ile Lys Gln Tyr Asn
                            725                 730                 735

ACA TTA ATA GAA GAA ATG CTT CAG GTC CTC ATC TAT ATT GTG GGA GAA         2373
Thr Leu Ile Glu Glu Met Leu Gln Val Leu Ile Tyr Ile Val Gly Glu
            740                 745                 750

CGT TAT GTA CCT GGA GTG GGA AAT GTT ACC AGA GAG GAG GTT ATA ATG         2421
Arg Tyr Val Pro Gly Val Gly Asn Val Thr Arg Glu Glu Val Ile Met
    755                 760                 765

AGA GAG ATT ACT CAC TTA CTT TGC ATT GAG CCC ATG CCA CAC AGT GCC         2469
Arg Glu Ile Thr His Leu Leu Cys Ile Glu Pro Met Pro His Ser Ala
770                 775                 780                 785

ATC GCC AGA AAC CTA CCT GAG AAC GAA AAT AAT GAA ACT GGC TTA GAG         2517
Ile Ala Arg Asn Leu Pro Glu Asn Glu Asn Asn Glu Thr Gly Leu Glu
                790                 795                 800

AAT GTC ATA AAC AAA GTG GCC ACA TTT AAG AAA CCA GGT GTG TCG GGC         2565
Asn Val Ile Asn Lys Val Ala Thr Phe Lys Lys Pro Gly Val Ser Gly
            805                 810                 815

CAT GGA GTT TAT GAA TTG AAA GAT GAA TCA CTG AAA GAC TTC AAT ATG         2613
His Gly Val Tyr Glu Leu Lys Asp Glu Ser Leu Lys Asp Phe Asn Met
    820                 825                 830

TAC TTT TAC CAT TAT TCT AAA ACA CAG CAT AGC AAG GCT GAA CAT ATG         2661
Tyr Phe Tyr His Tyr Ser Lys Thr Gln His Ser Lys Ala Glu His Met
835                 840                 845

CAG AAG AAA AGG AGA AAA CAA GAA AAT AAA GAT GAA GCA TTG CCG CCG         2709
Gln Lys Lys Arg Arg Lys Gln Glu Asn Lys Asp Glu Ala Leu Pro Pro
850                 855                 860                 865

CCA CCT CCT CCA GAG TTC TGC CCT GCT TTC AGC AAA GTA GTC AAC CTG         2757
Pro Pro Pro Pro Glu Phe Cys Pro Ala Phe Ser Lys Val Val Asn Leu
                870                 875                 880

CTC AGC TGT GAT GTT ATG ATA TAC ATC CTC AGG ACC ATC TTT GAG CGG         2805
Leu Ser Cys Asp Val Met Ile Tyr Ile Leu Arg Thr Ile Phe Glu Arg
            885                 890                 895

GCA GTG GAC ACG GAG TCT AAT CTG TGG ACA GAA GGG ATG CTG CAG ATG         2853
Ala Val Asp Thr Glu Ser Asn Leu Trp Thr Glu Gly Met Leu Gln Met
    900                 905                 910

GCG TTC CAT ATA TTG GCA CTG GGC TTG CTG GAA GAG AAG CAG CAG CTT         2901
Ala Phe His Ile Leu Ala Leu Gly Leu Leu Glu Glu Lys Gln Gln Leu
915                 920                 925

CAG AAA GCT CCT GAA GAG GAA GTG GCT TTT GAC TTT TAC CAT AAA GCT         2949
Gln Lys Ala Pro Glu Glu Glu Val Ala Phe Asp Phe Tyr His Lys Ala
930                 935                 940                 945

TCA AGA TTG GGA AGT TCA GCC ATG AAT GCT CAG AAT ATA CAA ATG CTC         2997
Ser Arg Leu Gly Ser Ser Ala Met Asn Ala Gln Asn Ile Gln Met Leu
                950                 955                 960

TTG GAA AGA CTC AAA GGA ATC CCC CAA TTA GAA GGC CAG AAG GAC ATG         3045
Leu Glu Arg Leu Lys Gly Ile Pro Gln Leu Glu Gly Gln Lys Asp Met
            965                 970                 975

ATA ACA TGG ATA CTC CAG ATG TTT GAC ACA GTG AAG CGA TTA AGA GAA         3093
Ile Thr Trp Ile Leu Gln Met Phe Asp Thr Val Lys Arg Leu Arg Glu
    980                 985                 990

AAA TCT TGT TTA GTT GTG GCA ACC ACT TCA GGA CTG GAG TGC ATT AAG         3141
Lys Ser Cys Leu Val Val Ala Thr Thr Ser Gly Leu Glu Cys Ile Lys
995                 1000                1005

AGT GAG GAG ATT ACT CAT GAT AAA GAA AAG GCA GAA CGG AAG AGA AAA         3189
Ser Glu Glu Ile Thr His Asp Lys Glu Lys Ala Glu Arg Lys Arg Lys
1010                1015                1020                1025

GCT GAG GCC GCT AGG CTT CAT CGC CAG AAG ATC ATG GCC CAG ATG TCT         3237
Ala Glu Ala Ala Arg Leu His Arg Gln Lys Ile Met Ala Gln Met Ser
                1030                1035                1040
```

```
GCC TTA CAG AAA AAC TTC ATT GAA ACC CAC AAA CTC ATG TAT GAT AAT      3285
Ala Leu Gln Lys Asn Phe Ile Glu Thr His Lys Leu Met Tyr Asp Asn
            1045                1050                1055

ACG TCA GAA GTA ACA GGG AAG GAA GAC TCC ATT ATG GAG GAA GAG AGC      3333
Thr Ser Glu Val Thr Gly Lys Glu Asp Ser Ile Met Glu Glu Glu Ser
        1060                1065                1070

ACC TCA GCA GTC AGT GAG GCC TCT AGA ATT GCT CTG GGC CCT AAA CGG      3381
Thr Ser Ala Val Ser Glu Ala Ser Arg Ile Ala Leu Gly Pro Lys Arg
        1075                1080                1085

GGC CCG GCT GTT ACC GAA AAG GAG GTG CTG ACG TGC ATC CTC TGC CAA      3429
Gly Pro Ala Val Thr Glu Lys Glu Val Leu Thr Cys Ile Leu Cys Gln
1090                1095                1100                1105

GAA GAA CAA GAG GTA AAA CTA GAA AAT AAT GCC ATG GTA TTG TCA GCA      3477
Glu Glu Gln Glu Val Lys Leu Glu Asn Asn Ala Met Val Leu Ser Ala
                1110                1115                1120

TGT GTG CAG AAA TCC ACC GCC CTA ACC CAG CAC AGA GGG AAG CCT GTG      3525
Cys Val Gln Lys Ser Thr Ala Leu Thr Gln His Arg Gly Lys Pro Val
            1125                1130                1135

GAC CAC TTA GGG GAA ACA CTG GAC CCT CTT TTC ATG GAT CCA GAC TTG      3573
Asp His Leu Gly Glu Thr Leu Asp Pro Leu Phe Met Asp Pro Asp Leu
        1140                1145                1150

GCA CAT GGA ACT TAT ACA GGA AGC TGT GGT CAT GTA ATG CAT GCA GTG      3621
Ala His Gly Thr Tyr Thr Gly Ser Cys Gly His Val Met His Ala Val
        1155                1160                1165

TGC TGG CAG AAG TAT TTT GAA GCT GTG CAG CTG AGC TCG CAG CAG CGC      3669
Cys Trp Gln Lys Tyr Phe Glu Ala Val Gln Leu Ser Ser Gln Gln Arg
1170                1175                1180                1185

ATT CAC GTA GAC CTG TTT GAC CTG GAG AGC GGC GAG TAC CTA TGC CCG      3717
Ile His Val Asp Leu Phe Asp Leu Glu Ser Gly Glu Tyr Leu Cys Pro
                1190                1195                1200

CTC TGC AAG TCT CTC TGC AAC ACT GTC ATC CCC ATC ATC CCT TTG CAG      3765
Leu Cys Lys Ser Leu Cys Asn Thr Val Ile Pro Ile Ile Pro Leu Gln
            1205                1210                1215

CCG CAG AAG ATC AAC AGT GAG AAT GCG GAG GCT CTT GCT CAA CTT TTG      3813
Pro Gln Lys Ile Asn Ser Glu Asn Ala Glu Ala Leu Ala Gln Leu Leu
        1220                1225                1230

ACC TTG GCC CGG TGG ATA CAG ACT GTC CTT GCC AGA ATA TCG GGT TAT      3861
Thr Leu Ala Arg Trp Ile Gln Thr Val Leu Ala Arg Ile Ser Gly Tyr
        1235                1240                1245

AAT ATA AAG CAT GCT AAA GGA GAA GCC CCA GCA GTT CCT GTC TTG TTT      3909
Asn Ile Lys His Ala Lys Gly Glu Ala Pro Ala Val Pro Val Leu Phe
1250                1255                1260                1265

AAT CAA GGA ATG GGG GAT TCA ACT TTT GAG TTT CAT TCC ATC CTG AGT      3957
Asn Gln Gly Met Gly Asp Ser Thr Phe Glu Phe His Ser Ile Leu Ser
                1270                1275                1280

TTT GGA GTT CAG TCT TCG GTG AAA TAT TCA AAT AGT ATC AAG GAA ATG      4005
Phe Gly Val Gln Ser Ser Val Lys Tyr Ser Asn Ser Ile Lys Glu Met
            1285                1290                1295

GTC ATT CTC TTC GCC ACA ACA ATT TAC AGA ATT GGC CTG AAA GTG CCT      4053
Val Ile Leu Phe Ala Thr Thr Ile Tyr Arg Ile Gly Leu Lys Val Pro
        1300                1305                1310

CCT GAT GAA CTA GAC CCA CGA GTG CCC ATG ATG ACC TGG AGC ACG TGT      4101
Pro Asp Glu Leu Asp Pro Arg Val Pro Met Met Thr Trp Ser Thr Cys
        1315                1320                1325

GCG TTC ACC ATC CAG GCA ATC GAA AAC CTG TTG GGA GAT GAA GGA AAA      4149
Ala Phe Thr Ile Gln Ala Ile Glu Asn Leu Leu Gly Asp Glu Gly Lys
1330                1335                1340                1345

CCT CTA TTT GGA GCA CTT CAA AAT AGA CAG CAT AGC GGT CTG AAG GCG      4197
Pro Leu Phe Gly Ala Leu Gln Asn Arg Gln His Ser Gly Leu Lys Ala
                1350                1355                1360
```

-continued

```
CTA ATG CAG TTT GCA GTT GCA CAG AGG GCT ACC TGC CCT CAG GTC CTG      4245
Leu Met Gln Phe Ala Val Ala Gln Arg Ala Thr Cys Pro Gln Val Leu
        1365                1370                1375

ATA CAC AAA CAT CTG GCT CGG CTC CTG TCA GTT ATT CTT CCT AAC CTG      4293
Ile His Lys His Leu Ala Arg Leu Leu Ser Val Ile Leu Pro Asn Leu
            1380                1385                1390

CAA TCA GAA AAT ACA CCA GGC CTT CTG TCT GTG GAT CTC TTC CAT GTT      4341
Gln Ser Glu Asn Thr Pro Gly Leu Leu Ser Val Asp Leu Phe His Val
        1395                1400                1405

CTG GTC GGC GCA GTC TTA GCG TTC CCA TCC TTG TAT TGG GAT GAC ACC      4389
Leu Val Gly Ala Val Leu Ala Phe Pro Ser Leu Tyr Trp Asp Asp Thr
1410                1415                1420                1425

GTG GAT CTG CAG CCG TCG CCA CTT AGT TCT TCA TAT AAC CAC CTC TAT      4437
Val Asp Leu Gln Pro Ser Pro Leu Ser Ser Ser Tyr Asn His Leu Tyr
                1430                1435                1440

CTC TTC CAT CTG ATC ACC ATG GCG CAC ATG CTT CAG ATA CTC CTT ACA      4485
Leu Phe His Leu Ile Thr Met Ala His Met Leu Gln Ile Leu Leu Thr
        1445                1450                1455

ACA GAT ACA GAT CTG TCT CCA GGG CCG CCG CTT GCT GAG GGT GAA GAG      4533
Thr Asp Thr Asp Leu Ser Pro Gly Pro Pro Leu Ala Glu Gly Glu Glu
            1460                1465                1470

GAT AGT GAG GAG GCT CGC TGT GCA TCT GCT TTC TTT GTG GAA GTG TCG      4581
Asp Ser Glu Glu Ala Arg Cys Ala Ser Ala Phe Phe Val Glu Val Ser
        1475                1480                1485

CAG CAC ACA GAC GGC CTC ACT GGG TGC GGT GCT CCC GGC TGG TAC CTG      4629
Gln His Thr Asp Gly Leu Thr Gly Cys Gly Ala Pro Gly Trp Tyr Leu
1490                1495                1500                1505

TGG CTC TCC CTG AGG AAC GGC ATC ACC CCT TAC CTC CGC TGT GCT GCA      4677
Trp Leu Ser Leu Arg Asn Gly Ile Thr Pro Tyr Leu Arg Cys Ala Ala
                1510                1515                1520

CTG CTT TTC CAC TAT TTA CTT GGA GTA GCT CCG CCT GAA GAA CTG TTT      4725
Leu Leu Phe His Tyr Leu Leu Gly Val Ala Pro Pro Glu Glu Leu Phe
        1525                1530                1535

GCC AAT TCT GCT GAA GGA GAA TTC AGT GCA CTC TGT AGC TAT CTA TCT      4773
Ala Asn Ser Ala Glu Gly Glu Phe Ser Ala Leu Cys Ser Tyr Leu Ser
            1540                1545                1550

TTA CCC ACA AAT TTG TTC CTG CTT TTC CAG GAA TAT TGG GAT ACC ATA      4821
Leu Pro Thr Asn Leu Phe Leu Leu Phe Gln Glu Tyr Trp Asp Thr Ile
        1555                1560                1565

AGG CCC TTA CTA CAG AGG TGG TGT GGA GAT CCT GCC TTA CTC AAG TCT      4869
Arg Pro Leu Leu Gln Arg Trp Cys Gly Asp Pro Ala Leu Leu Lys Ser
1570                1575                1580                1585

TTG AAG CAG AAA AGT GCT GTG GTC AGG TAC CCT AGA AAA AGA AAT AGT      4917
Leu Lys Gln Lys Ser Ala Val Val Arg Tyr Pro Arg Lys Arg Asn Ser
                1590                1595                1600

TTG ATA GAG CTT CCT GAG GAC TAC AGC TGT CTT CTA AAT CAG GCT TCT      4965
Leu Ile Glu Leu Pro Glu Asp Tyr Ser Cys Leu Leu Asn Gln Ala Ser
        1605                1610                1615

CAC TTT AGG TGT CCA CGG TCT GCA GAT GAT GAG CGA AAG CAT CCT GTC      5013
His Phe Arg Cys Pro Arg Ser Ala Asp Asp Glu Arg Lys His Pro Val
            1620                1625                1630

CTC TGT CTT TTC TGT GGG GCC ATC CTG TGT TCT CAG AAC ATC TGT TGC      5061
Leu Cys Leu Phe Cys Gly Ala Ile Leu Cys Ser Gln Asn Ile Cys Cys
        1635                1640                1645

CAA GAA ATA GTG AAT GGG GAA GAG GTT GGA GCG TGC GTT TTT CAT GCG      5109
Gln Glu Ile Val Asn Gly Glu Glu Val Gly Ala Cys Val Phe His Ala
1650                1655                1660                1665

CTT CAT TGT GGT GCT GGA GTC TGC ATT TTC CTA AAA ATC CGA GAA TGC      5157
Leu His Cys Gly Ala Gly Val Cys Ile Phe Leu Lys Ile Arg Glu Cys
```

-continued

```
                 1670              1675              1680
AGG GTG GTC CTG GTG GAA GGA AAA GCC AGA GGC TGT GCC TAC CCA GCC    5205
Arg Val Val Leu Val Glu Gly Lys Ala Arg Gly Cys Ala Tyr Pro Ala
             1685              1690              1695

CCT TAC TTG GAT GAA TAT GGA GAA ACA GAC CCA GGG CTA AAG AGA GGA    5253
Pro Tyr Leu Asp Glu Tyr Gly Glu Thr Asp Pro Gly Leu Lys Arg Gly
             1700              1705              1710

AAC CCA CTT CAT TTA TCT CGG GAG CGG TAT CGG AAG CTG CAT TTG GTC    5301
Asn Pro Leu His Leu Ser Arg Glu Arg Tyr Arg Lys Leu His Leu Val
             1715              1720              1725

TGG CAA CAG CAC TGC ATT ATA GAA GAG ATT GCT CGG AGC CAG GAG ACT    5349
Trp Gln Gln His Cys Ile Ile Glu Glu Ile Ala Arg Ser Gln Glu Thr
1730              1735              1740              1745

AAT CAG ATG CTA TTT GGA TTT AAC TGG CAG TTA CTC TGAGCTTCAG         5395
Asn Gln Met Leu Phe Gly Phe Asn Trp Gln Leu Leu
             1750              1755

TTCTGCCTCA AGACAATCAT GAGTGACATC AATAATAAAG ACTGATCTAA AATTCTAGAG  5455

AACTTTCTGA GGACGGGGGA AGTATTGGAG GGTCTTTTGA TCCATGTCCA GATTCACACA  5515

CATTAATAAA ATATTCCTTA ATGGAATATT GCTTTCAATT ATCAAACATA AGCTTCAAGG  5575

GAAAACAAG ACATAGATTA ATGTTTTATG TTCTAGAACA CTAAAGAAAT GCTTGTTCAT   5635

CCAAGTGTCT ATTTCTGCTA ATATTTCCAG AAAACTCCTT TCCCTTCATA ACTGTCCTAG  5695

TTCATTTCAT ATCACCCACC TGGTTAATGA GGTCACATTA AGCATTTGTG ACATTTCTC   5755

CATCTGGCTA ACATCTCTGC ACCTTTGTAT TTGGTGTTTC TCGAGTGTAG TTTAGCTTGG  5815

GTTAGATCTC TGAAAAGATG CTGATCACCT GTGATGGTCT AAAGAGGAAT TGCACAACTA  5875

TGCAGTTTCT TTCAATTAAA AATTTCAAAA CATGTAAACA TCTTTCTTCT TTAAGGAAAT  5935

ATCCTTATTG TACCACCTAC GGCTTCAGTC AGAAACAGAT CTAAATCTCT CTATGGAGAG  5995

TGCTAGCTGT GCTAGTCTGG AAAGCATCCT TCCAGTGTAG ACCTCAAGTA GATTCAGGAG  6055

AATGTGCTCA TTACGCATTC CTTATACAAA ATCCTGTTAT CCTCACCTGA TTCCAGGGAG  6115

CTCTGTGGAG TCACAAGTTC TCCATCAGTT ACATTTCTTA AGGCAGATTT CTGCAGTAAG  6175

ATCTCGTCTC TTGGGGCCCC ATCCTATTGT CTCTCAGAAA ACTCTTGTTT TGAAGCAAAC  6235

TCTTTGTAGA ATGGGAATCA GAAAATTGCC CCAGTGAATG GTCATAAGAG ATGAAATTAG  6295

AACACTGTAT TTAAGCCAGT CTGCAACCCT TCTATGGCTT GTAAGAAACA GGTCCTTGAT  6355

TTGATGTCTA GGTGAAACCT TTCATAAACG ACTGTTTATG                       6395
```

(2) INFORMATION FOR SEQ ID NO:2:

(i) SEQUENCE CHARACTERISTICS:
        (A) LENGTH: 1001 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..999

(xi) SEQUENCE DESCRIPTION: SEQ ID NO:2:

```
ATG GAT CCC AAC AAG TTC TTG TTA CTG GTA CTT CAG AGG TAT GAA CTT    48
Met Asp Pro Asn Lys Phe Leu Leu Leu Val Leu Gln Arg Tyr Glu Leu
1               5                  10                 15

GCC GAG GCT TTT AAC AAG ACC ATA TCT ACA AAA GAC CAG GAT TTG ATT    96
Ala Glu Ala Phe Asn Lys Thr Ile Ser Thr Lys Asp Gln Asp Leu Ile
```

-continued

|  |  |  |  | 20 |  |  |  |  | 25 |  |  |  |  | 30 |  |  |  |
|---|---|---|---|---|---|---|---|---|---|---|---|---|---|---|---|---|---|

```
AAA CAA TAT AAT ACA CTA ATA GAA GAA ATG CTT CAG GTC CTC ATC TAT      144
Lys Gln Tyr Asn Thr Leu Ile Glu Glu Met Leu Gln Val Leu Ile Tyr
             35                  40                  45

ATT GTG GGT GAG CGT TAT GTA CCT GGA GTG GGA AAT GTG ACC AAA GAA      192
Ile Val Gly Glu Arg Tyr Val Pro Gly Val Gly Asn Val Thr Lys Glu
         50                  55                  60

GAG GTC ACA ATG AGA GAA ATC ATT CAC TTG CTT TGC ATT GAA CCC ATG      240
Glu Val Thr Met Arg Glu Ile Ile His Leu Leu Cys Ile Glu Pro Met
 65                  70                  75                  80

CCA CAC AGT GCC ATT GCC AAA AAT TTA CCT GAG AAT GAA AAT AAT GAA      288
Pro His Ser Ala Ile Ala Lys Asn Leu Pro Glu Asn Glu Asn Asn Glu
                 85                  90                  95

ACT GGC TTA GAG AAT GTC ATA AAC AAA GTG GCC ACA TTT AAG AAA CCA      336
Thr Gly Leu Glu Asn Val Ile Asn Lys Val Ala Thr Phe Lys Lys Pro
            100                 105                 110

GGT GTA TCA GGC CAT GGA GTT TAT GAA CTA AAA GAT GAA TCA CTG AAA      384
Gly Val Ser Gly His Gly Val Tyr Glu Leu Lys Asp Glu Ser Leu Lys
        115                 120                 125

GAC TTC AAT ATG TAC TTT TAT CAT TAC TCC AAA ACC CAG CAT AGC AAG      432
Asp Phe Asn Met Tyr Phe Tyr His Tyr Ser Lys Thr Gln His Ser Lys
    130                 135                 140

GCT GAA CAT ATG CAG AAG AAA AGG AGA AAA CAA GAA AAC AAA GAT GAA      480
Ala Glu His Met Gln Lys Lys Arg Arg Lys Gln Glu Asn Lys Asp Glu
145                 150                 155                 160

GCA TTG CCG CCA CCA CCA CCT CCT GAA TTC TGC CCT GCT TTC AGC AAA      528
Ala Leu Pro Pro Pro Pro Pro Pro Glu Phe Cys Pro Ala Phe Ser Lys
                165                 170                 175

GTG ATT AAC CTT CTC AAC TGT GAT ATC ATG ATG TAC ATT CTC AGG ACC      576
Val Ile Asn Leu Leu Asn Cys Asp Ile Met Met Tyr Ile Leu Arg Thr
            180                 185                 190

GTA TTT GAG CGG GCA ATA AAC ACA GAT TCT AAC TTG TGG ACC GAA GGG      624
Val Phe Glu Arg Ala Ile Asn Thr Asp Ser Asn Leu Trp Thr Glu Gly
        195                 200                 205

ATG CTC CAA ATG GCT TTT CAT ATT CTG GCA TTG GGT TTA CTA GAA GAG      672
Met Leu Gln Met Ala Phe His Ile Leu Ala Leu Gly Leu Leu Glu Glu
    210                 215                 220

AAG CAA CAG CTT CAA AAA GCT CCT GAA GAA GAA GTA ACA TTT GAC TTT      720
Lys Gln Gln Leu Gln Lys Ala Pro Glu Glu Glu Val Thr Phe Asp Phe
225                 230                 235                 240

TAT CAT AAG GCT TCA AGA TTG GGA AGT TCA GCC ATG AAT ATA CAA ATG      768
Tyr His Lys Ala Ser Arg Leu Gly Ser Ser Ala Met Asn Ile Gln Met
                245                 250                 255

CTT TTG GAA AAA CTC AAA GGA ATT CCC CAG TTA GAA GGC CAG AAG GAC      816
Leu Leu Glu Lys Leu Lys Gly Ile Pro Gln Leu Glu Gly Gln Lys Asp
            260                 265                 270

ATG ATA ACG TGG ATA CTT CAG ATG TTT GAC ACA GTG AAG CGA TTA AGA      864
Met Ile Thr Trp Ile Leu Gln Met Phe Asp Thr Val Lys Arg Leu Arg
        275                 280                 285

GAA AAA TCT TGT TTA ATT GTA GCA ACC ACA TCA GGA TCG GAA TCT ATT      912
Glu Lys Ser Cys Leu Ile Val Ala Thr Thr Ser Gly Ser Glu Ser Ile
    290                 295                 300

AAG AAT GAT GAG ATT ACT CAT GAT AAA GAA AAA GCA GAA CGA AAA AGA      960
Lys Asn Asp Glu Ile Thr His Asp Lys Glu Lys Ala Glu Arg Lys Arg
305                 310                 315                 320

AAA GCT GAA GCT GCT AGG CTT CAT CGC CAG AAG ATC ATG GC              1001
Lys Ala Glu Ala Ala Arg Leu His Arg Gln Lys Ile Met
                325                 330
```